United States Patent
Zhu

(10) Patent No.: US 7,340,303 B2
(45) Date of Patent: Mar. 4, 2008

(54) EVOKED RESPONSE SENSING FOR ISCHEMIA DETECTION

(75) Inventor: Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 211 days.

(21) Appl. No.: 09/962,852

(22) Filed: Sep. 25, 2001

(65) Prior Publication Data

US 2003/0060854 A1   Mar. 27, 2003

(51) Int. Cl.
*A61N 1/37* (2006.01)
(52) U.S. Cl. ............................. 607/27; 607/28
(58) Field of Classification Search ............ 607/4, 607/9, 17, 18, 25–26, 28; 600/508–510, 600/512, 515–519
See application file for complete search history.

(56) References Cited

U.S. PATENT DOCUMENTS

| | | | |
|---|---|---|---|
| 3,692,027 A | 9/1972 | Ellinwood, Jr. | |
| 4,003,379 A | 1/1977 | Ellinwood, Jr. | |
| 4,146,029 A | 3/1979 | Ellinwood, Jr. | |
| 4,281,664 A | 8/1981 | Duggan | |
| 4,299,220 A | 11/1981 | Dorman | |
| 4,544,371 A | 10/1985 | Dormandy, Jr. et al. | |
| 4,556,063 A | 12/1985 | Thompson et al. | |
| 4,561,443 A | 12/1985 | Hogrefe et al. | |
| 4,674,518 A | 6/1987 | Salo | |
| 4,686,987 A | 8/1987 | Salo et al. | |
| 4,871,351 A | 10/1989 | Feingold | |
| 4,897,987 A | 2/1990 | Spalla | |
| 4,924,875 A | 5/1990 | Chamoun | |
| 4,930,075 A * | 5/1990 | Kortas ........................ 600/509 |
| 4,944,299 A | 7/1990 | Silvian | |
| 4,987,897 A | 1/1991 | Funke | |
| 5,014,698 A | 5/1991 | Cohen | |
| 5,040,533 A | 8/1991 | Fearnot | |
| 5,041,107 A | 8/1991 | Heil, Jr. | |
| 5,042,497 A | 8/1991 | Shapland | |
| 5,058,581 A | 10/1991 | Silvian | |
| 5,087,243 A | 2/1992 | Avitall | |
| 5,113,869 A * | 5/1992 | Nappholz et al. .......... 600/508 |
| 5,127,404 A | 7/1992 | Wyborny et al. | |
| 5,135,004 A * | 8/1992 | Adams et al. .............. 600/508 |
| 5,137,019 A | 8/1992 | Pederson et al. | |
| 5,184,614 A | 2/1993 | Collins et al. | |
| 5,190,035 A | 3/1993 | Salo et al. | |
| 5,199,428 A * | 4/1993 | Obel et al. .................... 607/44 |
| 5,220,917 A | 6/1993 | Cammilli et al. | |
| 5,269,301 A * | 12/1993 | Cohen ............................ 607/6 |
| 5,284,136 A | 2/1994 | Hauck et al. | |

(Continued)

FOREIGN PATENT DOCUMENTS

EP   0054138   6/1982

(Continued)

*Primary Examiner*—Kristen D. Mullen
(74) *Attorney, Agent, or Firm*—Schwegman, Lundberg, & Woessner, P.A.

(57) ABSTRACT

A cardiac pacemaker in which an electrogram is recorded from an evoked response sensing channel in order to detect changes indicative of cardiac ischemia. If such changes are detected, the maximum allowable pacing rate can be decreased for those pacing modes that allow the pacing rate to change with metabolic demand.

11 Claims, 3 Drawing Sheets

U.S. PATENT DOCUMENTS

| | | | |
|---|---|---|---|
| 5,305,745 A | 4/1994 | Zacouto | |
| 5,334,222 A | 8/1994 | Salo et al. | |
| 5,342,408 A | 8/1994 | deCoriolis et al. | |
| 5,353,800 A | 10/1994 | Pohndorf et al. | |
| 5,368,028 A | 11/1994 | Palti | |
| 5,391,190 A | 2/1995 | Pederson et al. | |
| 5,404,877 A | 4/1995 | Nolan et al. | |
| 5,416,695 A | 5/1995 | Stutman et al. | |
| 5,417,717 A | 5/1995 | Salo et al. | |
| 5,456,692 A | 10/1995 | Smith, Jr. et al. | |
| 5,460,605 A | 10/1995 | Tuttle et al. | |
| 5,487,752 A | 1/1996 | Salo et al. | |
| 5,496,360 A | 3/1996 | Hoffmann et al. | |
| 5,499,971 A | 3/1996 | Shapland et al. | |
| 5,531,768 A * | 7/1996 | Alferness | 607/6 |
| 5,540,728 A | 7/1996 | Shelton et al. | |
| 5,545,186 A | 8/1996 | Olson et al. | |
| 5,551,953 A | 9/1996 | Lattin et al. | |
| 5,556,421 A | 9/1996 | Prutchi et al. | |
| 5,562,713 A | 10/1996 | Silvian | |
| 5,579,876 A | 12/1996 | Adrian et al. | |
| 5,584,868 A | 12/1996 | Salo et al. | |
| 5,586,556 A | 12/1996 | Spivey et al. | |
| 5,591,215 A | 1/1997 | Greenhut et al. | |
| 5,603,331 A | 2/1997 | Heemels et al. | |
| 5,607,418 A | 3/1997 | Arzbaecher | |
| 5,607,463 A | 3/1997 | Schwartz et al. | |
| 5,632,766 A | 5/1997 | Hsu et al. | |
| 5,634,899 A | 6/1997 | Shapland et al. | |
| 5,662,689 A | 9/1997 | Elsberry et al. | |
| 5,683,424 A | 11/1997 | Brown et al. | |
| 5,690,682 A | 11/1997 | Buscemi et al. | |
| 5,693,075 A | 12/1997 | Plicchi et al. | |
| 5,703,125 A | 12/1997 | Bovy et al. | |
| 5,713,934 A * | 2/1998 | Leckrone | 607/28 |
| 5,720,770 A | 2/1998 | Nappholz et al. | |
| 5,730,125 A | 3/1998 | Prutchi et al. | |
| 5,766,229 A * | 6/1998 | Bornzin | 607/28 |
| 5,800,498 A | 9/1998 | Obino et al. | |
| 5,814,089 A | 9/1998 | Stokes et al. | |
| 5,817,131 A | 10/1998 | Elsberry et al. | |
| 5,833,603 A | 11/1998 | Kovacs et al. | |
| 5,836,935 A | 11/1998 | Ashton et al. | |
| 5,893,881 A | 4/1999 | Elsberry et al. | |
| 5,899,928 A | 5/1999 | Sholder et al. | |
| 5,925,066 A | 7/1999 | Kroll et al. | |
| 5,949,659 A | 9/1999 | Lesche | |
| 5,967,986 A | 10/1999 | Cimochowski et al. | |
| 5,991,668 A | 11/1999 | Leinders et al. | |
| 6,016,443 A | 1/2000 | Ekwall et al. | |
| 6,016,447 A | 1/2000 | Juran et al. | |
| 6,016,448 A | 1/2000 | Busacker et al. | |
| 6,021,350 A * | 2/2000 | Mathson | 607/17 |
| 6,022,322 A | 2/2000 | Prutchi | |
| 6,108,577 A | 8/2000 | Benser | 600/517 |
| 6,112,116 A | 8/2000 | Fischell et al. | |
| 6,112,117 A | 8/2000 | KenKnight et al. | |
| 6,115,636 A | 9/2000 | Ryan | |
| 6,128,526 A | 10/2000 | Stadler et al. | 600/517 |
| 6,140,740 A | 10/2000 | Porat et al. | |
| 6,141,588 A | 10/2000 | Cox et al. | |
| 6,154,675 A | 11/2000 | Juran et al. | |
| 6,155,267 A | 12/2000 | Nelson | |
| 6,161,042 A | 12/2000 | Hartley et al. | |
| 6,168,801 B1 | 1/2001 | Heil, Jr. et al. | |
| 6,198,394 B1 | 3/2001 | Jacobsen et al. | |
| 6,200,265 B1 | 3/2001 | Walsh et al. | |
| 6,203,495 B1 | 3/2001 | Bardy | |
| 6,206,914 B1 | 3/2001 | Soykan et al. | |
| 6,213,942 B1 | 4/2001 | Flach et al. | |
| 6,221,011 B1 | 4/2001 | Bardy | |
| 6,231,516 B1 | 5/2001 | Keilman et al. | |
| 6,237,398 B1 | 5/2001 | Porat et al. | |
| 6,251,125 B1 | 6/2001 | KenKnight et al. | |
| 6,254,573 B1 | 7/2001 | Haim et al. | |
| 6,256,233 B1 | 7/2001 | Glass | |
| 6,261,230 B1 | 7/2001 | Bardy | |
| 6,264,606 B1 | 7/2001 | Ekwall et al. | |
| 6,266,554 B1 | 7/2001 | Hsu et al. | |
| 6,270,457 B1 | 8/2001 | Bardy | |
| 6,272,377 B1 | 8/2001 | Sweeney et al. | |
| 6,277,072 B1 | 8/2001 | Bardy | |
| 6,277,078 B1 | 8/2001 | Porat et al. | |
| 6,278,894 B1 | 8/2001 | Salo et al. | |
| 6,280,380 B1 | 8/2001 | Bardy | |
| 6,298,272 B1 | 10/2001 | Peterfeso et al. | |
| 6,309,370 B1 | 10/2001 | Haim et al. | |
| 6,312,378 B1 | 11/2001 | Bardy | |
| 6,331,160 B1 | 12/2001 | Bardy | |
| 6,336,903 B1 | 1/2002 | Bardy | |
| 6,358,202 B1 | 3/2002 | Arent | |
| 6,358,203 B2 | 3/2002 | Bardy | |
| 6,361,522 B1 | 3/2002 | Scheiner et al. | |
| 6,361,780 B1 | 3/2002 | Ley et al. | |
| 6,368,284 B1 | 4/2002 | Bardy | |
| 6,370,424 B1 | 4/2002 | Prutchi | |
| 6,398,728 B1 | 6/2002 | Bardy | |
| 6,411,840 B1 | 6/2002 | Bardy | |
| 6,424,847 B1 | 7/2002 | Mastrototaro et al. | |
| 6,438,419 B1 | 8/2002 | Callaway et al. | |
| 6,440,066 B1 | 8/2002 | Bardy | |
| 6,442,413 B1 | 8/2002 | Silver | |
| 6,443,949 B2 | 9/2002 | Altman | |
| 6,453,195 B1 | 9/2002 | Thompson | |
| 6,459,917 B1 | 10/2002 | Gowda et al. | |
| 6,459,929 B1 | 10/2002 | Hopper et al. | |
| 6,468,263 B1 | 10/2002 | Fischell et al. | |
| 6,478,737 B2 | 11/2002 | Bardy | |
| 6,501,983 B1 | 12/2002 | Natarajan et al. | |
| 6,511,477 B2 | 1/2003 | Altman et al. | |
| 6,518,245 B1 | 2/2003 | Anderson et al. | |
| 6,539,256 B1 | 3/2003 | KenKnight et al. | |
| 6,604,000 B2 * | 8/2003 | Lu | 607/17 |
| 6,628,985 B2 | 9/2003 | Sweeney et al. | |
| 6,645,145 B1 | 11/2003 | Dreschel et al. | |
| 6,689,117 B2 | 2/2004 | Sweeney et al. | |
| 2001/0000802 A1 | 5/2001 | Soykan et al. | |
| 2002/0026228 A1 | 2/2002 | Schauerte | |
| 2002/0099328 A1 | 7/2002 | Scheiner et al. | |
| 2003/0004403 A1 | 1/2003 | Drinan et al. | |
| 2003/0045805 A1 | 3/2003 | Sheldon et al. | |
| 2003/0060854 A1 | 3/2003 | Qingsheng | |
| 2003/0069606 A1 | 4/2003 | Girouard et al. | |
| 2003/0158584 A1 | 8/2003 | Cates et al. | |
| 2003/0233132 A1 | 12/2003 | Pastore et al. | |
| 2004/0002739 A1 | 1/2004 | Cates et al. | |
| 2004/0059391 A1 | 3/2004 | Sweeney et al. | |
| 2004/0073262 A1 | 4/2004 | Lovett | |
| 2004/0093034 A1 | 5/2004 | Girouard et al. | |

FOREIGN PATENT DOCUMENTS

| | | |
|---|---|---|
| EP | 0467695 A2 | 1/1992 |
| EP | 0545628 A2 | 6/1993 |
| EP | 1050265 | 11/2000 |
| WO | WO-97/33513 | 9/1997 |
| WO | WO-9834537 A1 | 8/1998 |
| WO | WO-0007497 A1 | 2/2000 |

* cited by examiner

EVOKED RESPONSE SENSING FOR ISCHEMIA DETECTION

FIELD OF THE INVENTION

This invention pertains to systems and methods for cardiac rhythm management. In particular, the invention relates to cardiac pacemakers and their methods of operation.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The term "pacemaker" as used herein, however, should be taken to mean both pacemakers and any device with a pacing functionality, such as an implantable cardioverter/defibrillator with a pacemaker incorporated therein.

The most common condition for which pacemakers are used is the treatment of bradycardia where the intrinsic heart rate is too slow. The two most common causes of ventricular bradycardia are AV block and sick sinus syndrome. Permanent pacing for bradycardia is indicated in patients with symptomatic bradycardia of any type as long as it is likely to be permanent or recurrent and is not associated with a transient condition from which the patient may recover. In chronotropically competent patients (i.e., those patients whose atrial rhythm is responsive to metabolic demand) in need of ventricular pacing, atrial triggered modes such as DDD or VDD are desirable because they allow the pacing to track the physiologically normal atrial rhythm, which causes cardiac output to be responsive to the metabolic needs of the body.

In pacemaker patients who are chronotropically incompetent (e.g., sinus node dysfunction) or in whom atrial tracking modes such as DDD and VDD are contraindicated due to atrial arrhythmias, the heart rate is dictated solely by the pacemaker in the absence of faster intrinsic cardiac activity. That pacing rate is determined by the programmed escape intervals of the pacemaker and is referred to as the lower rate limit or LRL. Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise (e.g., due to increased venous return and increased myocardial contractility), the resulting increase in cardiac output is usually not sufficient to meet the body's metabolic needs unless the heart rate is also increased. If the heart is paced at a constant rate, severe limitations are imposed upon the patient with respect to lifestyle and activities. It is to overcome these limitations and improve the quality of life of such patients that rate-adaptive pacemakers have been developed. In a rate-adaptive pacemaker, the patient's metabolic demand is estimated with an exertion level sensor such as an accelerometer or minute-ventilation sensor. The sensed exertion level is then mapped to a sensor-indicated rate that becomes the lower rate limit for the pacemaker.

Rate-adaptive pacing is generally considered to be contraindicated for patients with known coronary artery disease (CAD) since the increase in heart rate brought about by rate-adaptive pacing also increases the oxygen demand of the heart. If the heart becomes ischemic due to insufficient blood flow in the face of increased oxygen demand, chest pain (angina pectoris) or triggering of an arrhythmia may result. For the same reasons, atrial tracking ventricular pacing modes may also be contraindicated in certain patients where cardiac ischemia results from atrial tracking pacing at high rates. Some pacemaker patients, however, may have undetected CAD with asymptomatic silent ischemia or may develop CAD subsequent to pacemaker implantation. It would be beneficial if the pacemaker could detect episodes of cardiac ischemia in those patients in order to provide that information to a clinician and/or automatically adjust the operation of the pacemaker.

SUMMARY OF THE INVENTION

In a particular embodiment, the present invention is a cardiac pacemaker in which an electrogram is recorded from an evoked response sensing channel in order to detect a change indicative of cardiac ischemia. Such a detected change may then be logged as a clinically significant event and the recorded electrogram later downloaded to a clinician for analysis via an external programmer. Detection of ischemia may also be used to automatically adjust the pacing rate in pacing modes that allow the pacing rate to change with metabolic demand. For example, in atrial tracking pacing modes, the maximum tracking rate can be decreased so that the ventricles are paced at that rate even if the intrinsic atrial rate is higher. In rate-adaptive pacing modes, where an escape interval for pacing a heart chamber is adjusted in order to pace the chamber at a sensor-indicated rate based upon a sensed exertion level, the maximum allowable sensor-indicated rate can be decreased. The response factor of the rate response curve used for rate-adaptive pacing can also be adjusted to map a given exertion level to a lower sensor-indicated rate if cardiac ischemia is detected.

The electrogram for detection of ischemia is recorded from an evoked response sensing channel that senses the depolarization of the myocardium brought about by delivery of a pace. The evoked response sensing channel may be the sensing/pacing channel used for delivering the pace or another sensing channel, such as one dedicated for that purpose. In order to detect an ischemic change, the electrogram can be compared with a reference electrogram to see if an increased current of injury is present. The comparison may involve, for example, cross-correlating the recorded and reference electrograms or comparing ST segment amplitudes, slopes, or integrations with reference values.

DETAILED DESCRIPTION

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
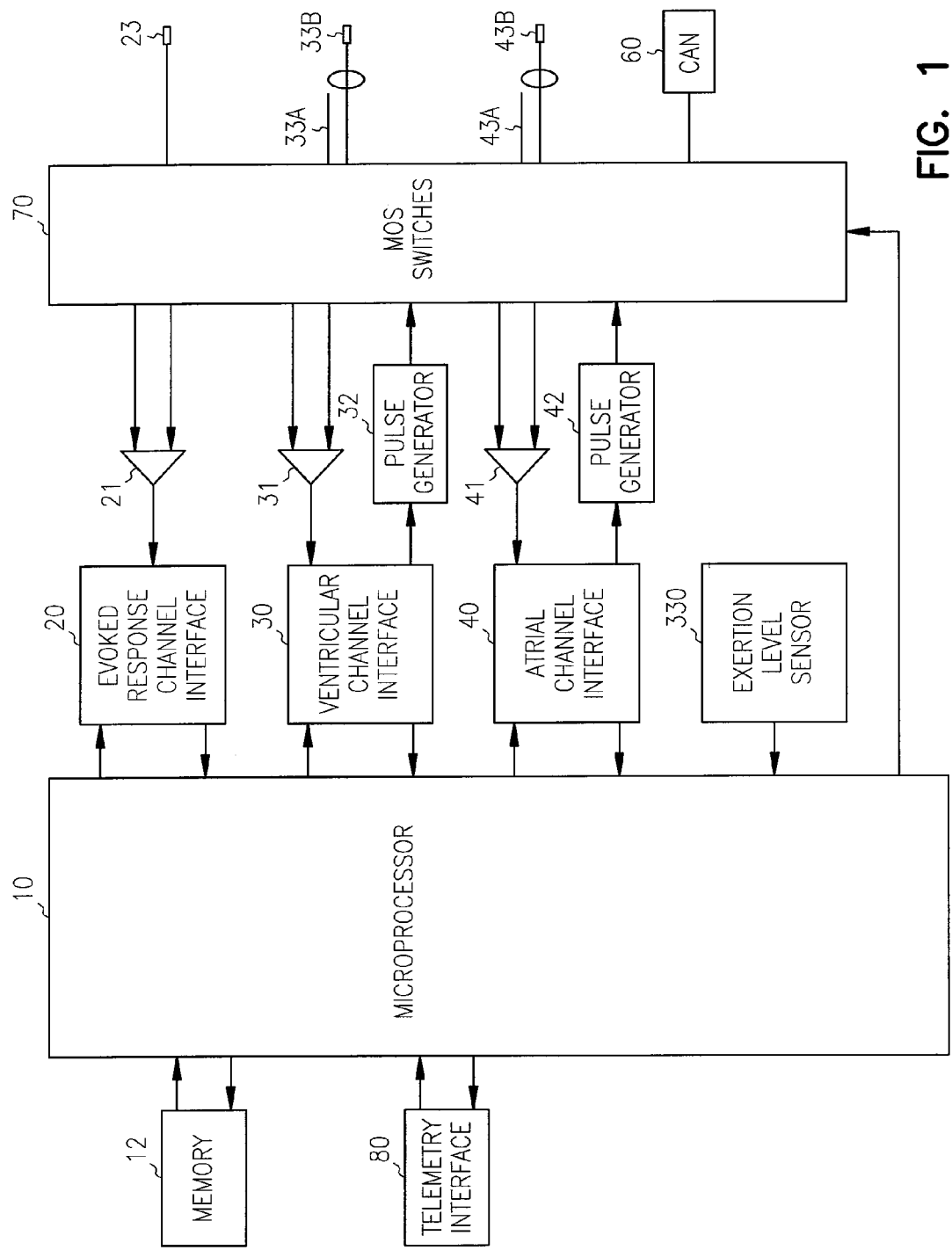
FIG. 1 is a block diagram of a rate-adaptive pacemaker.

The present invention may be incorporated into pacemakers having a number of different pacing configurations, including multi-site pacing configurations for delivering resynchronization therapy. For illustrative purposes, however, a block diagram of a dual-chamber pacemaker (i.e., one that sense and/or paces the atria and ventricles) is shown in FIG. 1. The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals.

The pacemaker has an atrial sensing/pacing channel comprising ring electrode 43a, tip electrode 43b, sense amplifier 41, pulse generator 42, and an atrial channel interface 40 which communicates bidirectionally with a port of microprocessor 10. The device also has a ventricular sensing/pacing channel that includes ring electrodes 33a, tip electrodes 33b, sense amplifier 31, pulse generator 32, and a ventricular channel interface 30. For each channel, the electrodes are connected to the pacemaker by a lead and used for both sensing and pacing. A MOS switching network 70 controlled by the microprocessor is used to switch the electrodes from the input of a sense amplifier to the output of a pulse generator. The pacemaker also has an evoked response sensing channel that comprises an evoked response channel interface 20 and a sense amplifier 21 that has its differential inputs connected to a unipolar electrode 23 and to the device housing or can 60 through the switching network 70. The evoked response sensing channel may be used to verify that a pacing pulse has achieved capture of the heart and caused a contraction or, as explained below, used to record an evoked response electrogram for detection of ischemia.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude. The microprocessor 10 controls the overall operation of the device in accordance with programmed instructions stored in memory. The sensing circuitry of the pacemaker generates atrial and ventricular sense signals when voltages sensed by the electrodes exceed a specified threshold. The controller then interprets sense signals from the sensing channels and controls the delivery of paces in accordance with a programmed pacing mode. An exertion level sensor 330 (e.g., an accelerometer or a minute ventilation sensor) enables the controller to adapt the pacing rate in accordance with changes in the patient's physical activity. The sense signals from any of the sensing channels of the pacemaker in FIG. 1 can be digitized and recorded by the controller to constitute an electrogram that can either be transmitted via a telemetry link 80 to an external programmer or stored for later transmission. The patient's cardiac activity may thus be observed in real-time or over a selected historical period.

In accordance with the invention, an electrogram can also be recorded of an evoked response to a pace and used to detect cardiac ischemia. An evoked response is the wave of depolarization that results from a pacing pulse and, since it evidences that the paced chamber has responded appropriately and contracted, it can be used to verify that the pace has achieved capture of the heart. Sensing channels in a pacemaker that provide senses for controlling pacing are commonly rendered refractory (i.e., insensitive) for a specified time period immediately following a pace in order to prevent the pacemaker from mistaking a pacing pulse or afterpotential for an intrinsic beat. This is done by the pacemaker controller ignoring sensed events during the refractory intervals, which are defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channel is used for both sensing intrinsic activity to control pacing and for sensing an evoked response, a period for sensing an evoked response should preferably be defined that supercedes any normal refractory period of the sensing channel.

An evoked response sensing channel for recording an electrogram can be a sensing channel used for other purposes which is adapted for sensing evoked responses or can be a sensing channel dedicated to sensing evoked responses. In order to detect ischemic changes in an electrogram, it is preferable to record the electrogram with a unipolar electrode that "sees" a larger volume of the myocardium as a wave of electrical activity spreads than a bipolar electrode. In the embodiment illustrated in FIG. 1, the atrial and ventricular sensing pacing channels utilize bipolar electrodes, and a dedicated evoked response sensing channel is provided with a unipolar electrode. Alternate embodiments may employ unipolar electrodes in the atrial and/or sensing/ pacing channels, in which case unipolar sensing of an evoked response may be performed with those channels instead of a dedicated channel.

In order to detect whether the patient is experiencing cardiac ischemia during pacing, the controller is programmed to analyze the recorded electrogram of an evoked response and look for a "current of injury." When the blood supply to a region of the myocardium is compromised, the supply of oxygen and other nutrients can become inadequate for enabling the metabolic processes of the cardiac muscle cells to maintain their normal polarized state. An ischemic region of the heart therefore becomes abnormally depolarized during at least part of the cardiac cycle and causes a current to flow between the ischemic region and the normally polarized regions of the heart, referred to as a current of injury. A current of injury may be produced by an infarcted region that becomes permanently depolarized or by an ischemic region that remains abnormally depolarized during all or part of the cardiac cycle. A current of injury results in an abnormal change in the electrical potentials measured by either a surface electrocardiogram or an intracardiac electrogram. If the abnormal depolarization in the ventricles lasts for the entire cardiac cycle, a zero potential is measured only when the rest of ventricular myocardium has depolarized, which corresponds to the time between the end of the QRS complex and the T wave in an electrogram and is referred to as the ST segment. After repolarization of the ventricles, marked by the T wave in an electrogram, the measured potential is influenced by the current of injury and becomes shifted, either positively or negatively depending upon the location of the ischemic or infarcted region, relative to the ST segment. Traditionally, however, it is the ST segment that is regarded as shifted when an abnormal current of injury is detected by an electrogram or electrocardiogram. A current injury produced by an ischemic region that does not last for the entire cardiac cycle may only shift part of the ST segment, resulting in an abnormal slope of the segment. A current of injury may also be produced when ischemia causes a prolonged depolarization in a ventricular region which results in an abnormal T wave as the direction of the wave of repolarization is altered.

Figure 2:
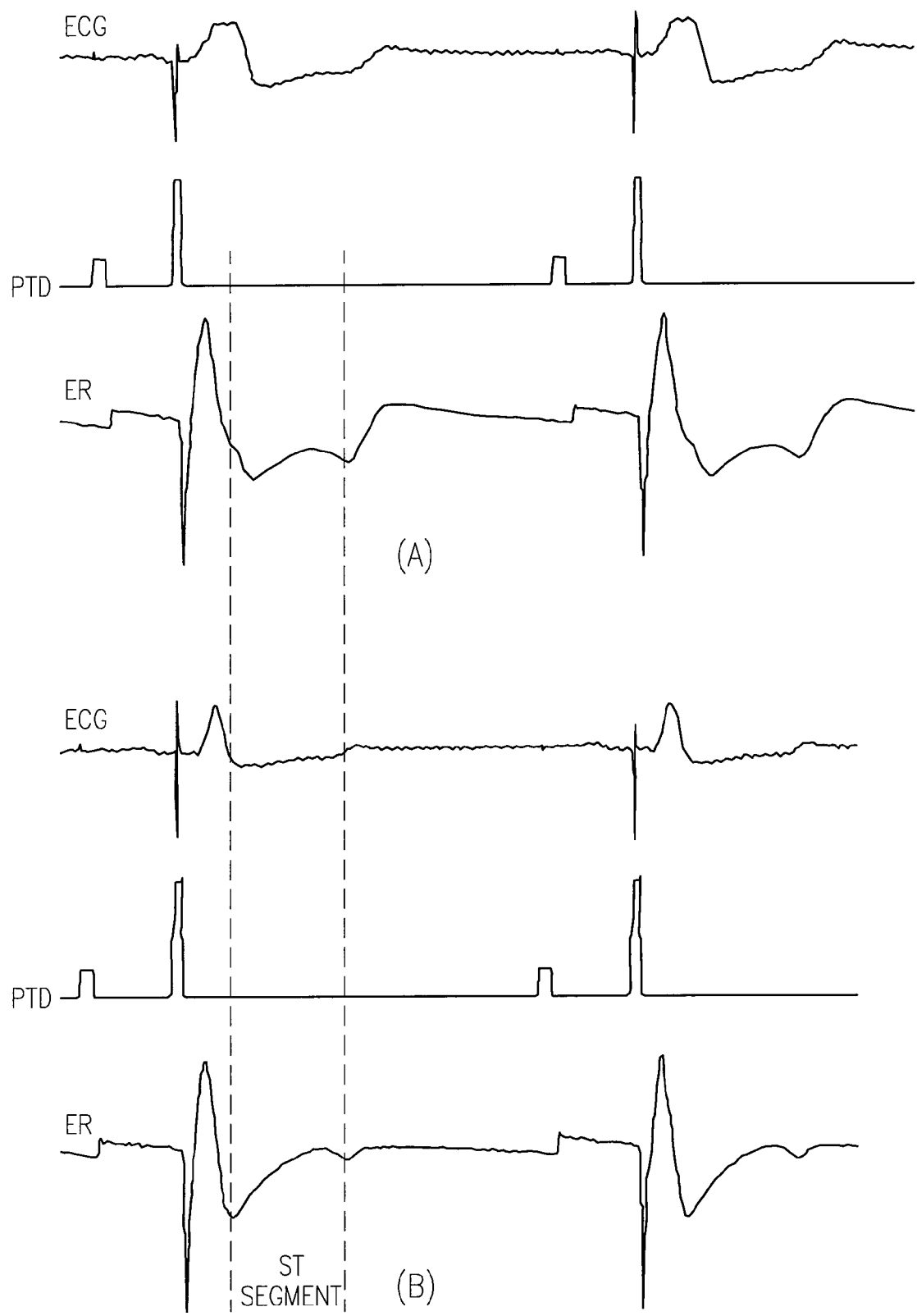
FIG. 2 illustrates ischemic changes in a recorded electrogram.

In order to detect a change in an electrogram indicative of ischemia, a recorded electrogram is analyzed and compared with a reference electrogram, which may either be a complete recorded electrogram or particular reference values representative of an electrogram. Because certain patients may always exhibit a current of injury in an electrogram (e.g., due to CAD or as a result of electrode implantation), the controller is programmed to detect ischemia by looking for an increased current of injury in the recorded electrogram as compared with the reference electrogram, where the latter may or may not exhibit a current of injury. FIG. 2 shows examples of evoked response data for two cases labeled A and B, where A is the baseline reference and B is during an acute ischemic episode. A surface electrocardiogram labeled ECG, a pacing timing diagram labeled PTD, and an electrogram labeled ER are illustrated for each case. The ST segment of the electrogram for case B is seen to have a different amplitude and slope as compared with the amplitude and slope of the ST segment of the electrogram for case A. One way to look for an increased current of injury in the recorded electrogram is to compare the ST segment amplitude and/or slope with the amplitude and slope of a reference electrogram. Various digital signal processing techniques may be employed for the analysis, such as using first and second derivatives to identify the start and end of an ST segment. Other ways of looking for a current injury may involve, for example, cross-correlating the recorded and reference electrograms to ascertain their degree of similarity. The electrogram could be implicitly recorded in that case by passing the electrogram signal through a matched filter that cross-correlates the signal with a reference electrogram. The ST segment could also be integrated, with the result of the integration compared with a reference value to determine if an increased current of injury is present.

If a change in a recorded electrogram indicative of ischemia is detected, the change may be logged as a clinically significant event in the pacemaker's memory. The event log and/or the recorded electrogram exhibiting the ischemia may then be later downloaded to a clinician for analysis via an external programmer. The clinician is then able to use this information in making subsequent treatment decisions. Detection of ischemia may also be used to automatically adjust the pacing rate in pacing modes that allow the pacing rate to change with metabolic demand. In an atrial tracking mode, for example, one or both ventricles are paced after expiration of a programmed atrio-ventricular interval if no preceding ventricular sense occurs, where the atrio-ventricular interval begins with an atrial sense. The pacing of the ventricles thus tracks the intrinsic atrial rate which, in a chronotropically competent patient, is responsive to metabolic demand. For safety reasons, a maximum tracking rate is usually programmed into an atrial tracking mode that limits the rate at which the ventricles can be paced regardless of the atrial rate. When ischemia is detected by the pacemaker, the controller may be programmed to automatically decrease the maximum tracking rate so that the ventricles are paced at that rate even if the intrinsic atrial rate is higher. Decreasing of the maximum tracking rate may thus prevent exacerbation of the ischemia from pacing at too high a rate.

Figure 3:
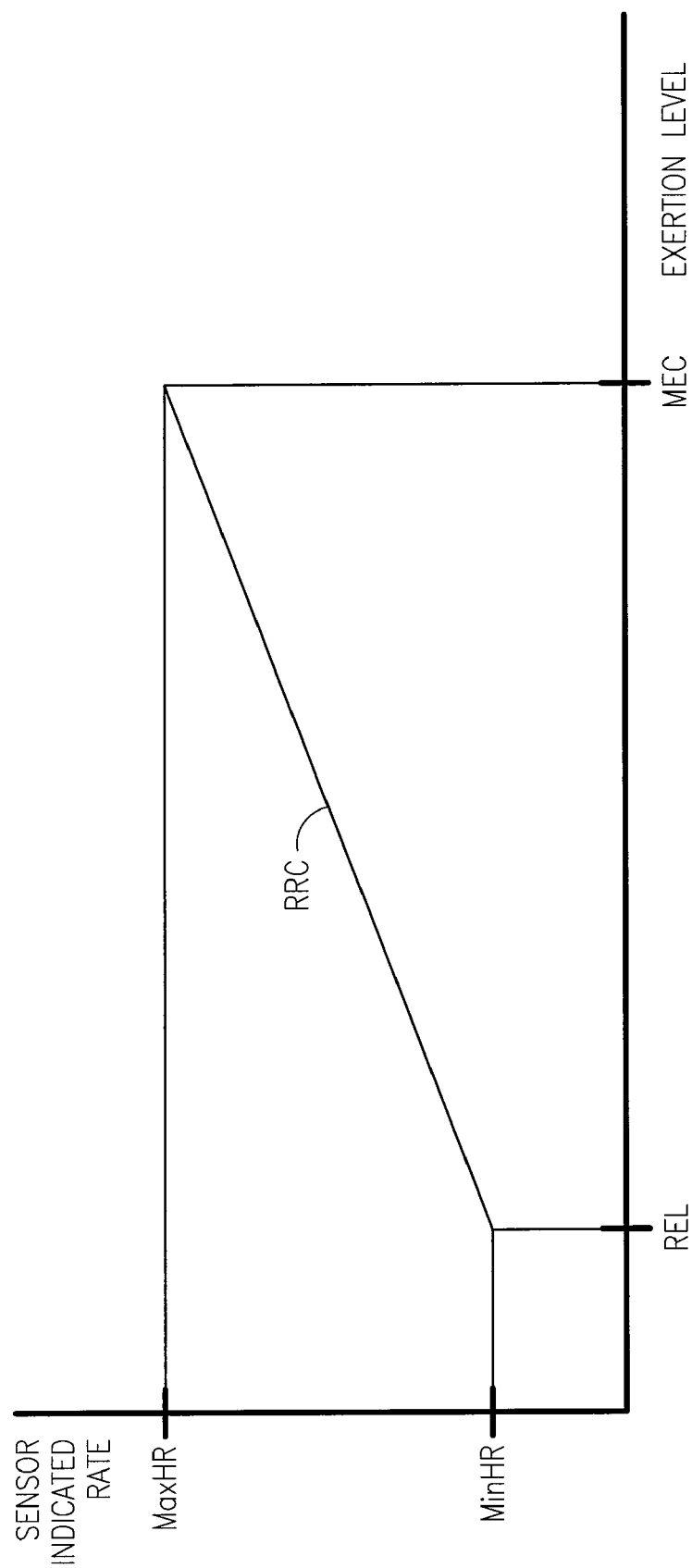
FIG. 3 is a diagram of a single-slope rate response curve.

Automatic adjustment of the maximum pacing rate when cardiac ischemia is detected may also be employed in rate-adaptive pacing. Rate-adaptive pacemakers modulate the ventricular and/or atrial escape intervals based upon measurements corresponding to physical activity and are applicable to situations in which atrial tracking modes cannot be used. In a rate-adaptive pacemaker operating in a ventricular pacing mode, the LRL is adjusted in accordance with exertion level measurements such as from an accelerometer or minute ventilation sensor in order for the heart rate to more nearly match metabolic demand. The adjusted LRL is then termed the sensor-indicated rate. The responsiveness of a rate-adaptive pacemaker is controlled in accordance with a rate-response curve RRC such as shown in FIG. 3. Other embodiments may use a dual-slope curve or a non-linear curve. A change in exertion level as determined from a minute ventilation measurement causes a proportional change in the sensor indicated rate in accordance with the slope of the curve, termed the response factor RF. The sensor indicated rate is then used as a lower rate limit (LRL) by the pacemaker to pace the heart in accordance with a programmed pacing mode, where the LRL is the rate at which the heart is paced in the absence of faster intrinsic activity. As shown in the figure, the rate response curve maps a resting exertion level REL to a minimum sensor indicated rate MinHR which corresponds to the minimum LRL that is to be used by the pacemaker. The maximum sensor indicated rate MaxHR is the maximum rate at which the pacemaker is allowed to pace the heart and is mapped to by the rate response curve from the maximum exertion level the patient is expected to be able to reach, referred to as the maximum exercise capacity MEC. When cardiac ischemia is detected from a recorded electrogram, the controller may be programmed to decrease the maximum allowable sensor-indicated rate MaxHR. The response factor of the rate response curve can also be adjusted to map a given exertion level to a lower sensor-indicated rate if cardiac ischemia is detected.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for operating a cardiac pacemaker, comprising:

sensing intrinsic cardiac activity in one or more cardiac chambers from a sensing channel;

delivering paces to a cardiac chamber in accordance with a programmed pacing mode;

recording an evoked response electrogram from the sensing channel when a pace is delivered;

storing a representation of a previously recorded reference evoked response electrogram that indicates any baseline current of injury;

looking for an increased current of injury by cross-correlating the recorded electrogram with the reference electrogram in order to detect a change indicative of ischemia; and, adjusting one or more pacing parameters that reduce the extent of pacing if a change indicative of cardiac ischemia is detected.

2. The method of claim 1 further comprising:

sensing an exertion level and mapping the sensed exertion level to a particular sensor-indicated rate with a rate-response curve;

adjusting an escape interval in order to enforce the sensor-indicated rate; and, wherein the specified maximum pacing rate is a maximum sensor-indicated rate.

3. The method of claim 2 further comprising adjusting the rate-response curve so that a particular exertion level is mapped to a lower sensor-indicated rate if a change in the electrogram indicative of cardiac ischemia is detected.

4. The method of claim 1 wherein the paced heart chamber is a ventricle and the programmed pacing mode is an atrial tracking mode such that a ventricular pace is delivered after expiration of an atrio-ventricular interval without a ventricular sense, the atrio-ventricular interval being started by an atrial sense, and further comprising decreasing a maximum tracking rate that limits the rate at which ventricular paces can be delivered in response to atrial senses if a change in the recorded electrogram indicative of cardiac ischemia is detected.

5. The method of claim 1 wherein an increased current of injury is looked for by cross-correlating the recorded electrogram with the reference electrogram using a matched filter.

6. A cardiac pacemaker, comprising:

a sensing channel for sensing intrinsic cardiac activity and for sensing an evoked response to a pace;

a pacing channel for pacing a cardiac chamber;

a controller for delivering paces to the cardiac chamber in accordance with a programmed pacing mode wherein the controller is programmed to record an evoked response electrogram from the sensing channel when a pace is delivered;

wherein the controller is programmed to store a representation of a previously recorded reference evoked response electrogram that indicates any baseline current of injury;

wherein the controller is programmed to look for an increased current of injury by cross-correlating the recorded electrogram with the reference electrogram in order to detect a change indicative of cardiac ischemia; and, wherein the controller is programmed to adjust one or more pacing parameters that reduce the extent of pacing if a change indicative of cardiac ischemia is detected.

7. The pacemaker of claim 6 wherein the controller is further programmed to log a detected change in the electrogram indicative of cardiac ischemia as a clinically significant event.

8. The pacemaker of claim 6 further comprising an exertion level sensor and wherein the controller is further programmed to:

sense an exertion level and map the sensed exertion level to a particular sensor-indicated rate with a rate-response curve, wherein the sensor-indicated rate is limited to a specified maximum sensor-indicated rate;

adjust an escape interval in order to enforce the sensor-indicated rate; and, decrease the specified maximum sensor-indicated rate if a change in the recorded electrogram indicative of cardiac ischemia is detected.

9. The pacemaker of claim 5 wherein the controller is further programmed to adjust the response factor of the rate-response curve so that a particular exertion level is mapped to a lower sensor-indicated rate if a change in the electrogram indicative of cardiac ischemia is detected.

10. The pacemaker of claim 6 wherein the paced heart chamber is a ventricle and the programmed pacing mode is an atrial tracking mode such that a ventricular pace is delivered after expiration of an atrio-ventricular interval without a ventricular sense, the atrio-ventricular interval being started by an atrial sense, and further wherein the controller is programmed to decrease a maximum tracking rate that limits the rate at which ventricular paces can be delivered in response to atrial senses if a change in the recorded electrogram indicative of cardiac ischemia is detected.

11. The pacemaker of claim 6 wherein the controller is programmed to look for an increased current of injury by cross-correlating the recorded electrogram with the reference electrogram using a matched filter.

* * * * *

UNITED STATES PATENT AND TRADEMARK OFFICE
CERTIFICATE OF CORRECTION

| | | |
|---|---|---|
| PATENT NO. | : 7,340,303 B2 | Page 1 of 1 |
| APPLICATION NO. | : 09/962852 | |
| DATED | : March 4, 2008 | |
| INVENTOR(S) | : Zhu | |

It is certified that error appears in the above-identified patent and that said Letters Patent is hereby corrected as shown below:

In column 8, line 24, in Claim 9, delete "claim 5" and insert -- claim 8 --, therefor.

Signed and Sealed this

Sixteenth Day of March, 2010

David J. Kappos
*Director of the United States Patent and Trademark Office*